United States Patent
Marka

(10) Patent No.: US 7,311,410 B2
(45) Date of Patent: Dec. 25, 2007

(54) OPERATING TABLE LAMP

(75) Inventor: Rudolf Marka, Munich (DE)

(73) Assignee: Trumpf Kreuzer Medizin Systeme GmbH + Co. KG, Puchheim (DE)

( * ) Notice: Subject to any disclaimer, the term of this patent is extended or adjusted under 35 U.S.C. 154(b) by 9 days.

(21) Appl. No.: 11/067,581

(22) Filed: Feb. 28, 2005

(65) Prior Publication Data

US 2005/0195601 A1  Sep. 8, 2005

(30) Foreign Application Priority Data

Feb. 28, 2004  (EP) .................................. 04004600

(51) Int. Cl.
*A61G 13/00* (2006.01)

(52) U.S. Cl. ..................... 362/33; 362/252; 362/418; 362/804

(58) Field of Classification Search ................. 362/33, 362/252, 804, 800, 512, 418–430
See application file for complete search history.

(56) References Cited

U.S. PATENT DOCUMENTS

| | | | | |
|---|---|---|---|---|
| 2,093,457 | A * | 9/1937 | Kuklin | ........................ 362/142 |
| 2,134,551 | A * | 10/1938 | Enfield | ........................ 362/250 |
| 2,896,066 | A * | 7/1959 | Quetin | ........................ 362/33 |
| 3,225,184 | A * | 12/1965 | Heinz-Joachim | ............. 362/33 |
| 3,588,488 | A | 6/1971 | Lauterbach | |
| 4,196,460 | A | 4/1980 | Schreckendgust | |
| 4,380,794 | A | 4/1983 | Lawson | |
| 5,383,105 | A * | 1/1995 | Agut | ........................... 362/285 |
| 5,743,628 | A * | 4/1998 | Greif et al. | .................. 362/228 |
| 6,402,351 | B1 * | 6/2002 | Borders et al. | ............. 362/395 |
| 6,447,149 | B1 * | 9/2002 | Kaforey et al. | ............. 362/400 |
| 6,488,390 | B1 | 12/2002 | Lebens et al. | |
| 6,495,964 | B1 | 12/2002 | Muthu et al. | |
| 6,582,092 | B1 | 6/2003 | Marka | |
| 6,880,957 | B2 * | 4/2005 | Walters | ....................... 362/276 |
| 2003/0014834 | A1 | 1/2003 | Naughton | |
| 2003/0165055 | A1 | 9/2003 | Scholz | |

FOREIGN PATENT DOCUMENTS

| | | |
|---|---|---|
| DE | 19838627 | 3/2000 |
| DE | 10034594 | 1/2002 |
| FR | 1311965 | 12/1962 |
| GB | 819936 | 9/1959 |
| JP | 60-119936 | 6/1985 |
| WO | 03/019072 | 3/2003 |

* cited by examiner

*Primary Examiner*—Ali Alavi
*Assistant Examiner*—Gunyoung T. Lee
(74) *Attorney, Agent, or Firm*—Fish & Richardson P.C.

(57) ABSTRACT

An operating lamp includes a lamp body for receiving a light source, a first light source housed in the lamp body and adapted for illuminating an illumination area of an operating area, and a second light source housed in the lamp body and adapted for illuminating a central portion of the illumination area. The brightness of the second light source is controllable independently of the brightness of the first light source to enhance the brightness of the central portion of the illumination area.

7 Claims, 5 Drawing Sheets

OPERATING TABLE LAMP

CLAIM OF PRIORITY

This application claims priority under 35 USC § 119(a) to European Patent application number 04004600, filed on Feb. 28, 2004, the entire contents of which are hereby incorporated by reference.

TECHNICAL FIELD

This disclosure relates to an operating table lamp.

BACKGROUND

Conventional operating table lamps (e.g., as described in German Patent No. 198 38 627 A1) include at least one radiation source and at least two reflectors. To produce an illumination field from the lamp with few shadows, the radiation emitted by the operating lamp impinges onto the illumination field at least two different angles of incidence. The angles of incidence of the radiation can thereby be adjusted by changing the separation between at least two reflectors or between a reflector and the radiation source.

Prior art operating lamps cannot change of shape of the illuminated field (e.g., the illuminated area on the operating table) as may be required for individual applications.

Conventional operating lamps have a fixed light distribution. Operating lamps must meet the requirements given in various different illumination situations. For example, large-surface wounds require a large amount of light from the edge of the lamp to prevent shadows and provide light behind obstacles. For wounds with a smaller diameter and large depth, light from the center of the lamp is required. These extreme requirements are only poorly met by conventional operating lamps, because conventional lamps generally exhibit compromises with respect to light distribution.

For this reason, head lights are conventionally used today, as are optical fibers that can be introduced into the wound. However, a disadvantage of such light sources is that the head light or the optical fiber limits the operating surgeon (e.g., due to the un-ergonomic posture required of the operating surgeon to hold the head lamp) or limits the light power due to soiling and problems with hygiene when the light source is introduced into direct contact with the wound.

SUMMARY

The invention is based, at least in part, on the recognition that improved illumination of deep wounds of small diameter can be provided by controlling a light source in the center of an operating lamp separately from the actual light source, and changing (e.g., increasing) the brightness in the center of the operating lamp. A control means of the operating lamp can control the illumination means in the center of the operating lamp independently of other illumination means and can increase the brightness in the center of the lamp independently of the rest of the operating lamp. A separate light source can be provided in the center of the operating lamp. An additional light source can be disposed in a handle located in the center of the operating lamp.

In a general aspect, an operating lamp includes a lamp body for receiving a light source, a first light source housed in the lamp body and adapted for illuminating an illumination area of an operating area, and a second light source housed in the lamp body and adapted for illuminating a central portion of the illumination area. The brightness of the second light source is controllable independently of the brightness of the first light source to enhance the brightness of the central portion of the illumination area.

Implementations can include one or more of the following features. For example, the second light source can include a light module, and the first light source can include a plurality of light modules that surround the first light source. The operating lamp can further include a handle mounted approximately centrally in the lamp body, and the first light source can be annularly disposed around the handle. The second light source can be disposed in the handle. The operating lamp can further include a removable sleeve adapted for mounting on the handle, and the second light source can be housed in the removable sleeve.

The first light source and/or the second light source can include an LED. The operating lamp can further include a first lens adapted for widening a light beam from the first light source, and a second lens adapted for widening a light beam from the second light source.

In another general aspect, a method of illuminating an operating area includes providing light from a first light source housed in a lamp body to an illumination area on the operating area, providing light from a second light source housed in the lamp body to a central portion of the illumination area, and independently controlling a brightness of the second light source compared with a brightness of the second light source.

Implementations can include at least the following feature. For example, the method can further include directing light from the first light source to the illumination area in a first light beam, and directing light from the second light source to the illumination area in a second light beam, where a conical angle of the first light beam is greater than the conical angle of the second light beam.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
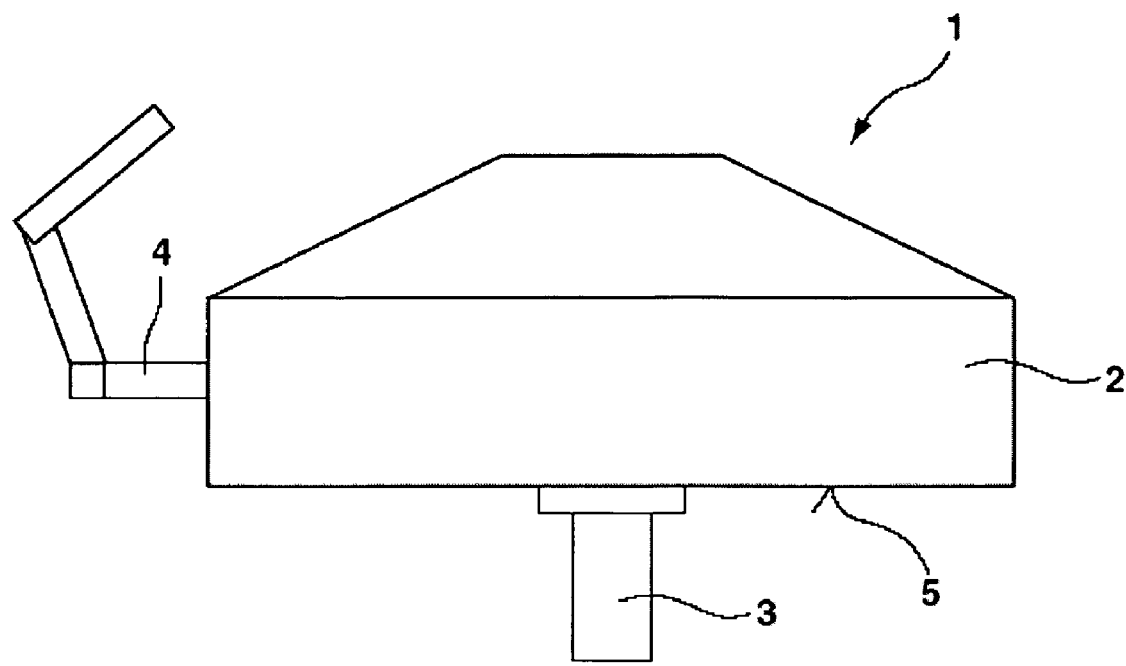
FIG. 1 is a schematic side view of an operating lamp.

As shown in FIG. 1, an operating lamp 1 includes a lamp body 2 having an inner space that houses an illumination means (not shown in FIG. 1). The lamp body 2 can be mounted on a stationary holder on a ceiling or wall of a building or on a mobile unit, such that it can be pivoted via a pivot arm (which is not completely shown in FIG. 1). The pivot arm is formed from several elements that are interconnected by joints. An element 4 of the pivot arm that is rigidly connected to the operating lamp 1 is indicated in FIG. 1. The operating lamp 1 can therefore be moved and pivoted in three dimensions in the X, Y, and Z directions. A handle 3 mounted to the lamp body 2 permits positioning of the operating lamp 1 at any location above an operating table. The handle 3 is detachably disposed on the lower side 5 of the operating lamp. Light is emitted on the lower side 5 of the operating lamp 1 to illuminate the area of an operation.

Figure 2:
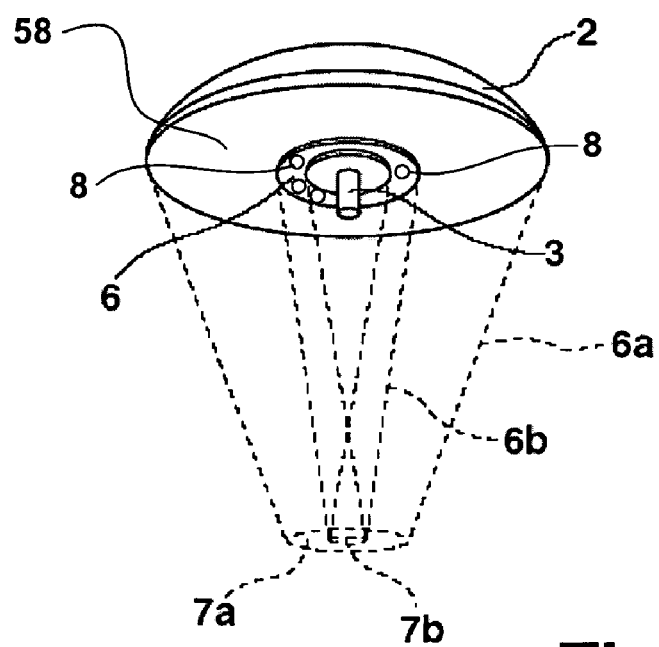
FIG. 2 is a schematic perspective view of a first switched-on operating lamp with depth illumination.

As shown in FIG. 2, an annular light source 6 includes several light emitting diodes 8 ("LEDs") mounted on the light emitting surface of the lamp body 2 around the edge of the handle 3. The handle 3 can be sterilized for use in an operating environment. The light source 6 generates an illumination field 7b with light beams 6b. The illumination field 7b supports an illumination field 7a of the operating lamp, which is generated by the light beams 6a. The illumination field 7a can be created by an additional light source 58 that is spans a surface area larger than the surface area of light source 6. For example, light source 58 can be a large mirror for reflecting light onto the illumination field 7a or can be one or more light source that radiate light directly onto illumination field 7a. Thus, the light beams of the light source 6 are focused to the center of the illumination field 7a, and the illumination field 7b improves the depth illumination in the center of the illumination field 7a. The intensity of the light source 6 may be correspondingly controlled to optimize the depth illumination.

Figure 3:
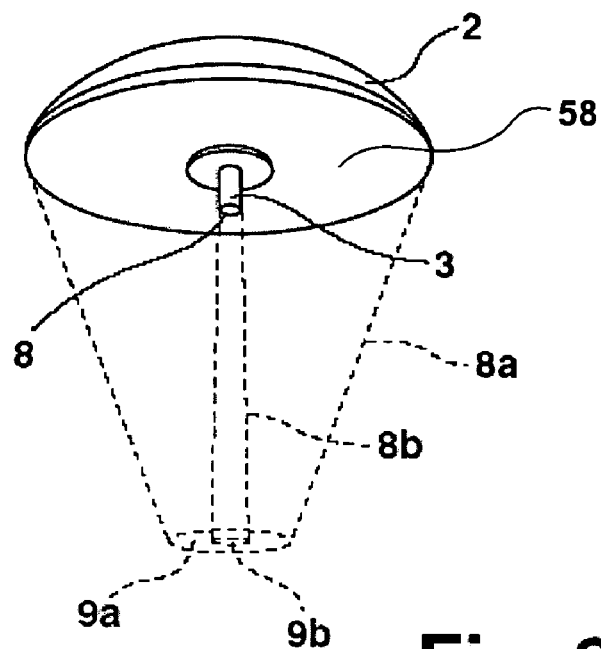
FIG. 3 is a schematic perspective view of a second switched-on operating lamp with depth illumination as provided by the invention.
Figure 4:
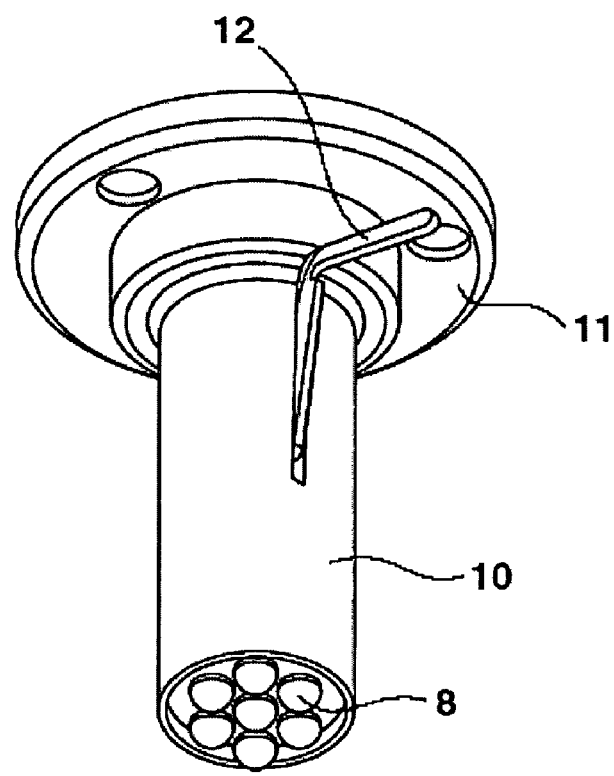
FIG. 4 is a schematic perspective view of a handle of the operating lamp shown in FIG. 3.

As shown in FIGS. 3 and 4, several LEDs 8 can be disposed as an additional light source 8 on the sterilizable central handle 3. Light beams 8b can be emitted by the light source 8 such that an additional illumination field 9b is generated in the center of the illumination field 9a that is generated by the light beams 8a from an additional light source 58.

As shown in FIG. 4, the handle 3 can include a sleeve 10 that can be detachably mounted to the operating lamp 1. The detachable sleeve 10 can be mounted to the operating lamp 1 via a flange 11, and the sterilizable handle 3 can be removed from the lamp body for cleaning and sterilization. Locking and release of the handle 3 from the operating lamp 1 can be achieved using an actuating element 12 that can release a catch. Several LEDs 8 that generate white light are disposed in a free end of the sleeve 10, such that light can be emitted from the sleeve 10. The light can be emitted through a bore in the handle 3, through a transparent window that optionally covers the bore, or through a handle of transparent material. To guide the beams in a parallel direction, the LEDs 8 can be associated with lens elements. The additional illumination from the light source 8 may be switched on as required.

Figure 5:
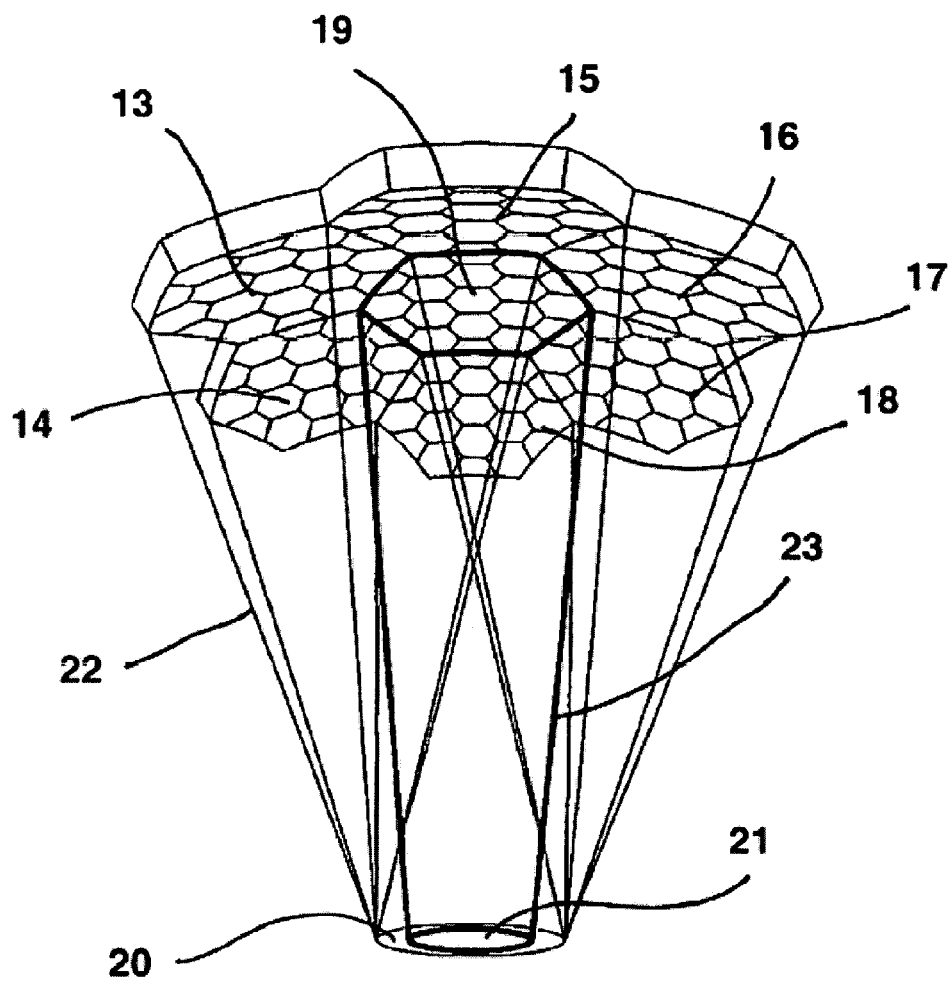
FIG. 5 is a schematic perspective view of a switched-on operating lamp with depth illumination.

As shown in FIG. 5, individual light modules 13–19, which can be combined in arbitrary combinations, can each include a plurality of LEDs for generating an illumination field 20. The intensity of light from the central light module 19 can be increased to produce a light beam 23 and an additional illumination field 21 that is superposed on the illumination field 20 from the light beam 22. The additional illumination field 21 from the central light module can be used to illuminate deep wounds.

Figure 6:
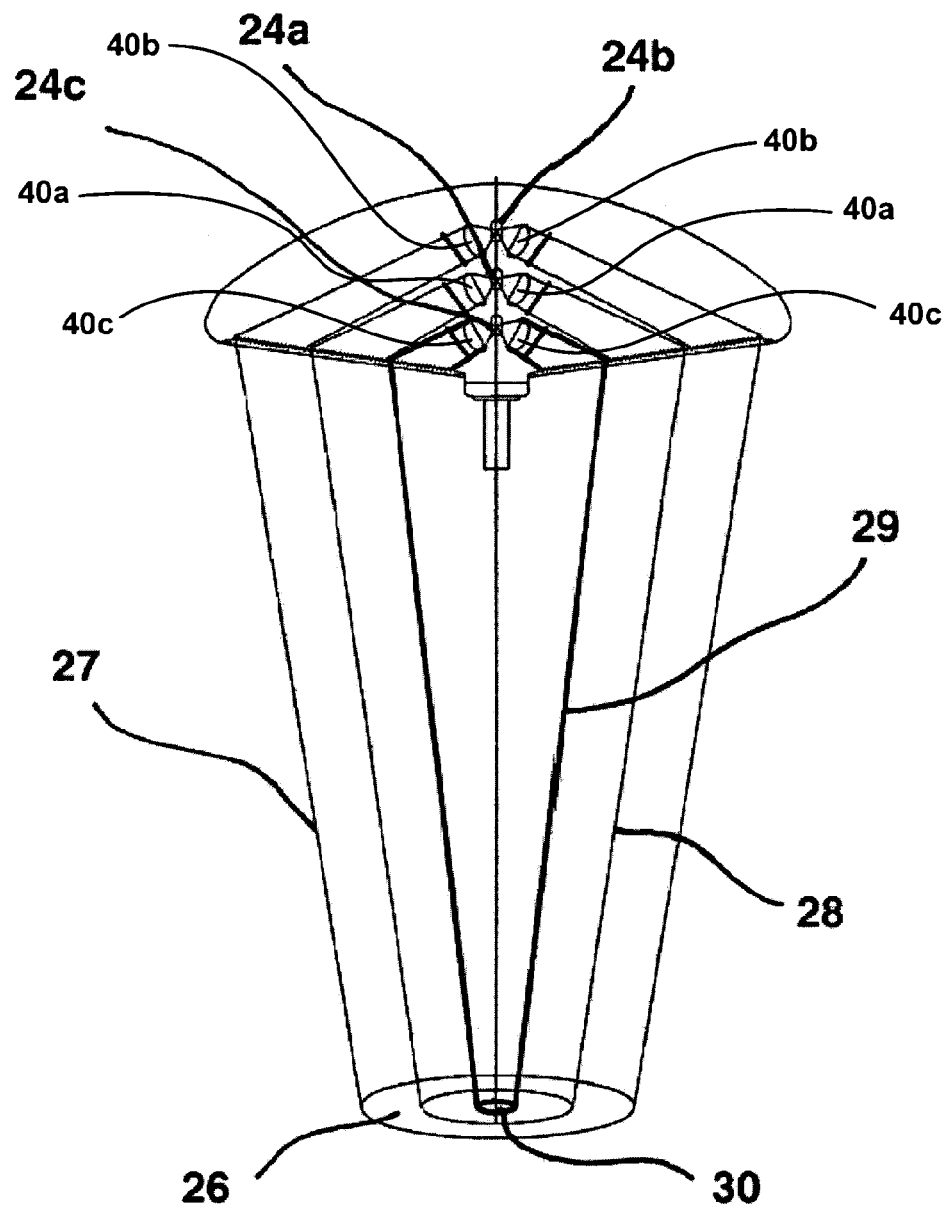
FIG. 6 is a schematic perspective view of a switched-on operating lamp with depth illumination.

As shown in FIG. 6, a light source can include individual illumination means 24a, 24b, and 24c that are surrounded by lenses 40a, 40b, and 40c provided to widen the light beams from the illumination means and to generate light beams 27–29 that create an illumination field 26. The intensity of the illumination field 26 can be increased in the center 30 by increasing the intensity of the light source 24c, such that the intensity of the central light beam 29 is higher than the radiation in the edge regions of the illumination field 26.

Figure 7:
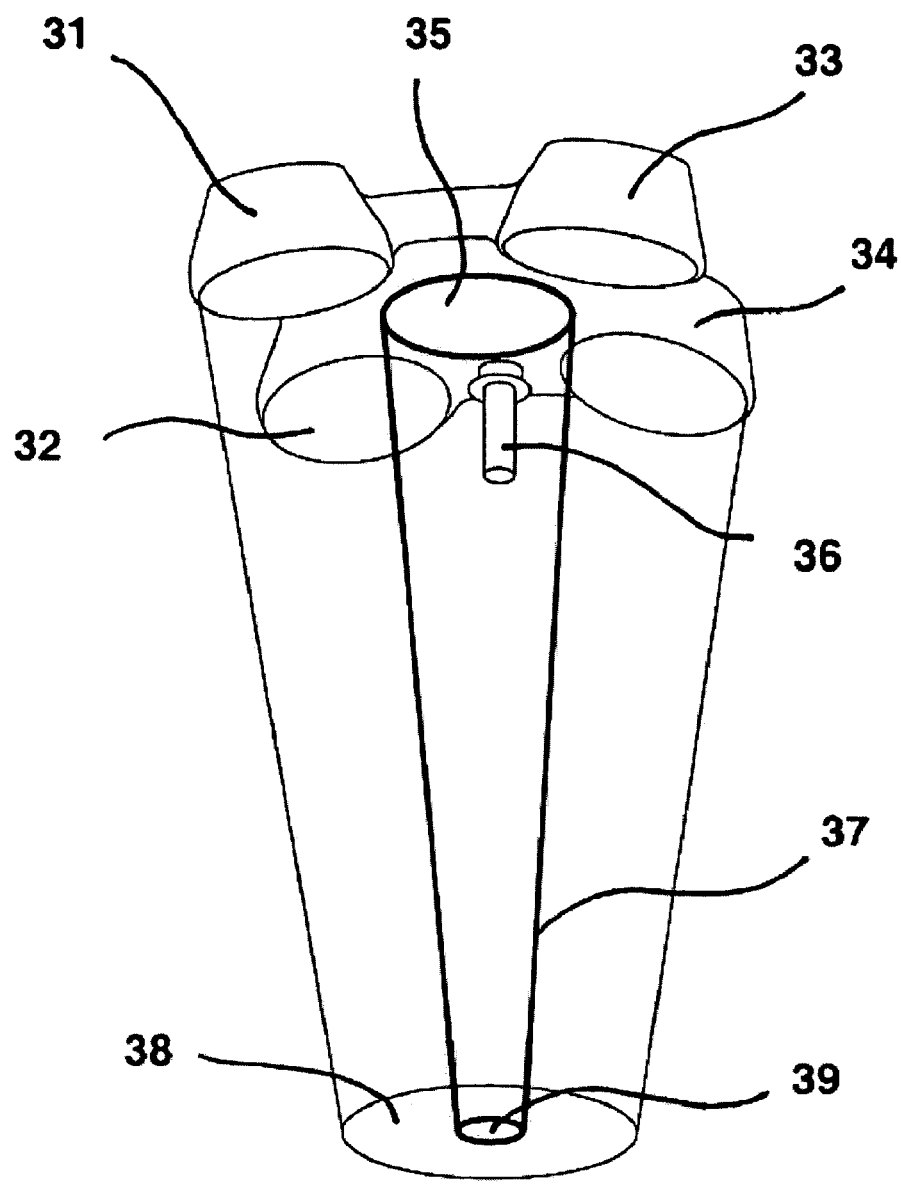
FIG. 7 is a schematic perspective view of a switched-on operating lamp with depth illumination.

As shown in FIG. 7, an operating lamp 1 can include a resolved light system formed by individual lamps 31–35 and a handle 36 disposed at the edge of the system. The central lamp 35 generates a light beam 37 having increased intensity compared with surrounding light, such that an illumination field 38 has a higher brightness in its center 39 than at its edges to illuminate deep wounds.

OTHER EMBODIMENTS

A number of embodiments of the invention have been described. Nevertheless, it will be understood that various modifications may be made. Accordingly, other embodiments are within the scope of the following claims.

What is claimed is:

1. A surgical operating lamp comprising:
 a surgical operating lamp body for receiving a light source;
 a first light source housed in the lamp body and illuminating an illumination area of an operating area; and
 a handle, mounted approximately centrally in the lamp body, the first light source being annularly disposed around the handle; and
 a second light source housed in the lamp body and disposed in the handle, the second light source being configured to illuminate a central portion of the operation area, the second light source being further configured so that the brightness of the second light source is controlled independently of the brightness of the first light source to increase the brightness of the second light source and thereby enhance the brightness of the central portion of the illumination area.

2. The operating lamp of claim 1, wherein the second light source comprises a light module and wherein the first light source comprises a plurality of light modules that surround the second light source.

3. The operating lamp of claim 1, further comprising a removable sleeve adapted for mounting on the handle, and wherein the second light source is housed in the removable sleeve.

4. The operating lamp of claim 1, wherein the first light source comprises an LED.

5. The operating lamp of claim 1, wherein the second source comprises an LED.

6. The operating lamp of claim 1, further comprising.
 a first lens adapted for widening a light beam from the first light source; and
 a second lens adapted for widening a light beam from the second light source.

7. The operating lamp of claim 1 further comprising a switch for turning the second light source off and on independently of the first light source.

* * * * *